(12) United States Patent
Vick et al.

(10) Patent No.: US 8,119,859 B2
(45) Date of Patent: Feb. 21, 2012

(54) TRANSFORMATION OF ALGAL CELLS

(75) Inventors: Bertrand Vick, Emeryville, CA (US); Oliver Kilian, Alameda, CA (US)

(73) Assignee: Aurora Algae, Inc., Hayward, CA (US)

( * ) Notice: Subject to any disclaimer, the term of this patent is extended or adjusted under 35 U.S.C. 154(b) by 51 days.

(21) Appl. No.: 12/480,611

(22) Filed: Jun. 8, 2009

(65) Prior Publication Data

US 2009/0317857 A1    Dec. 24, 2009

Related U.S. Application Data

(60) Provisional application No. 61/059,672, filed on Jun. 6, 2008.

(51) Int. Cl.
 C12N 15/82 (2006.01)
 C12N 15/87 (2006.01)
 C12N 1/12 (2006.01)
 C12N 15/53 (2006.01)
 C12N 15/54 (2006.01)
 A01H 13/00 (2006.01)

(52) U.S. Cl. ........ 800/293; 800/281; 800/296; 435/189; 435/194; 435/257.2; 435/470

(58) Field of Classification Search .................. None
 See application file for complete search history.

(56) References Cited

U.S. PATENT DOCUMENTS

| | | | |
|---|---|---|---|
| 1,926,780 A | 9/1933 | Lippincott | |
| 3,468,057 A | 9/1969 | Buisson | |
| 3,962,466 A | 6/1976 | Nakabayashi | |
| 4,003,337 A | 1/1977 | Moore | |
| 4,267,038 A | 5/1981 | Thompson | |
| 4,365,938 A | 12/1982 | Warinner | |
| 4,658,757 A | 4/1987 | Cook | |
| 5,105,085 A | 4/1992 | McGuire et al. | |
| 5,478,208 A | 12/1995 | Kasai | |
| 5,527,456 A | 6/1996 | Jensen | |
| 5,661,017 A * | 8/1997 | Dunahay et al. | 435/470 |
| 5,668,298 A * | 9/1997 | Waldron | 800/288 |
| 5,823,781 A | 10/1998 | Hitchcock et al. | |
| 6,027,900 A | 2/2000 | Allnutt et al. | |
| 6,117,313 A | 9/2000 | Goldman | |
| 6,143,562 A * | 11/2000 | Trulson et al. | 435/420 |
| 6,297,054 B1 | 10/2001 | Maliga et al. | |
| 6,372,460 B1 | 4/2002 | Gladue et al. | |
| 6,736,572 B2 | 5/2004 | Geraghty | |
| 6,831,040 B1 | 12/2004 | Unkefer et al. | |
| 6,871,195 B2 | 3/2005 | Ryan et al. | |
| 7,244,609 B2 | 7/2007 | Drocourt et al. | |
| 7,381,326 B2 | 6/2008 | Haddas | |
| 7,410,637 B2 | 8/2008 | Sayre et al. | |
| 7,547,551 B2 | 6/2009 | Schuler et al. | |
| 2003/0140021 A1 | 7/2003 | Ryan et al. | |
| 2003/0143743 A1 | 7/2003 | Schuler et al. | |
| 2003/0199490 A1 | 10/2003 | Antoni-Zimmermann et al. | |
| 2003/0211089 A1 | 11/2003 | Sayre et al. | |
| 2004/0161364 A1 | 8/2004 | Carlson | |
| 2004/0262219 A1 | 12/2004 | Jensen | |
| 2005/0064577 A1 | 3/2005 | Berzin | |
| 2005/0095569 A1 | 5/2005 | Franklin | |
| 2005/0124010 A1 | 6/2005 | Short et al. | |
| 2005/0170479 A1 | 8/2005 | Weaver et al. | |
| 2005/0181345 A1 | 8/2005 | Bradbury et al. | |
| 2005/0260553 A1 | 11/2005 | Berzin | |
| 2006/0031087 A1 | 2/2006 | Fox et al. | |
| 2006/0044259 A1 | 3/2006 | Hotelling et al. | |
| 2006/0045750 A1 | 3/2006 | Stiles | |
| 2006/0101535 A1 * | 5/2006 | Forster et al. | 800/278 |
| 2006/0122410 A1 | 6/2006 | Fichtali et al. | |
| 2006/0155558 A1 | 7/2006 | Corpening | |
| 2006/0166243 A1 | 7/2006 | Su et al. | |
| 2006/0192690 A1 | 8/2006 | Philipp | |
| 2007/0178451 A1 | 8/2007 | Deng et al. | |
| 2008/0118964 A1 | 5/2008 | Huntley et al. | |
| 2008/0120749 A1 | 5/2008 | Melis et al. | |
| 2008/0160488 A1 | 7/2008 | Younkes et al. | |
| 2008/0160591 A1 | 7/2008 | Willson et al. | |
| 2008/0194029 A1 | 8/2008 | Hegemann et al. | |
| 2008/0293132 A1 | 11/2008 | Goldman et al. | |

(Continued)

FOREIGN PATENT DOCUMENTS

CN      1627764      6/2005

(Continued)

OTHER PUBLICATIONS

Endo et al. The Journal of Antibiotics 41(2): 271-273 (1988).*
Schiedlmeier et al. Proceedings of the National Academy of Sciences USA 91(11): 5080-5084 (May 1994).*
Hallmann et al. The Plant Journal 17(1): 99-109 (Jan. 1999).*
Kureshy et al. Journal of the World Aquaculture Society 30(4): 473-480 (Dec. 1999).*
Molnar et al. Highly specific gene silencing by artificial microRNAs in the unicellular alga *Chlamydomonas reinhardtii*. Plant Jour. ePub Jan. 17, 2009 vol. 58 No. 1 pp. 157-164. Especially abstract.
Chen et al. Conditional Production of a Functional Fish Growth Hormonal in the Transgenic Line of *Nannochloropsis oculata* (*Eustigmatophyceae*). J. Phycol. Jun. 2008 vol. 44 No. 3 pp. 768-776. Especially abstract.
Nelson et al. Targeted Disruption of the NIT8 Gene in *Chlamydomonas reinhardtii*. Mol. Cell Bio. Oct. 1995, vol. 15, No. 10, pp. 5762-5769. Especially abstract and p. 5763 left col. para 2.

(Continued)

*Primary Examiner* — David T Fox
(74) *Attorney, Agent, or Firm* — Carr & Ferrell LLP

(57) ABSTRACT

Exemplary methods include a method for transforming an algal cell by preparing a transformation construct, preparing a particle for bombarding the algal cell, adhering the transformation construct to the particle, bombarding the algal cell with the particle, and growing the algal cell into a colony. The transformation construct is replicated within a nuclear genome of the algal cell and the growing of the algal cell is in a nutrient medium. Another exemplary method may include a method for genetically modifying an algal cell, by adding nucleic acid to the algal cell while the algal cell is suspended in a solution of low conductivity, introducing the nucleic acid into the algal cell by application of an electrical pulse resulting in a transformed algal cell, and selecting a colony that includes the transformed algal cell.

13 Claims, 7 Drawing Sheets

U.S. PATENT DOCUMENTS

| | | | |
|---|---|---|---|
| 2009/0029445 | A1 | 1/2009 | Eckelberry et al. |
| 2009/0061928 | A1 | 3/2009 | Lee et al. |
| 2009/0148931 | A1 | 6/2009 | Wilkerson et al. |
| 2009/0234146 | A1 | 9/2009 | Cooney et al. |
| 2009/0317878 | A1 | 12/2009 | Champagne et al. |
| 2009/0317904 | A1 | 12/2009 | Vick et al. |
| 2009/0319338 | A1 | 12/2009 | Parks et al. |
| 2009/0325270 | A1 | 12/2009 | Vick et al. |
| 2010/0068772 | A1 | 3/2010 | Downey |
| 2010/0100520 | A1 | 4/2010 | Dargue et al. |
| 2010/0198659 | A1 | 8/2010 | Meltzer et al. |
| 2010/0210003 | A1 | 8/2010 | King |
| 2010/0210832 | A1 | 8/2010 | Kilian et al. |
| 2010/0314324 | A1 | 12/2010 | Rice et al. |
| 2010/0323387 | A1 | 12/2010 | Bailey et al. |
| 2010/0330643 | A1 | 12/2010 | Kilian et al. |
| 2011/0059495 | A1 | 3/2011 | Bailey et al. |
| 2011/0091977 | A1 | 4/2011 | Kilian et al. |

FOREIGN PATENT DOCUMENTS

| | | |
|---|---|---|
| CN | 1867140 | 11/2006 |
| CN | 1956335 | 5/2007 |
| WO | WO2004106238 | 12/2004 |
| WO | WO2007084078 | 7/2007 |
| WO | WO2008060571 A2 | 5/2008 |
| WO | WO2008060571 A3 | 5/2008 |
| WO | WO2008060571 A8 | 5/2008 |

OTHER PUBLICATIONS

Janssen, et al. "Enclosed outdoor photobioreactors: light regime, photosynthetic efficiency, scale-up, and future prospects" Biotechnology and Bioengineering, vol. 81, No. 2, pp. 193-210, Jan. 20, 2003, Entire document, especially: Fig 4, p. 198 [online]. Retrieved from the Internet on [Oct. 5, 2010]. Retrieved from: <URL: http://onlinelibrary.wiley.com/doi/10.1002bit.10468/pdf.

Strzepek, et al., "Photosynthetic architecture differs in coastal and oceanie diatoms" Nature vol. 431, pp. 689-692, Oct. 7, 2004, Entire document, especially: abstract, p. 689, col. 2; p. 691, Table 1 [online] Retrieved from the Internet on [Oct. 5, 2010]. Retrieved from: URL:http://www.nature.com/nature/journal/v431/n7009/pdf/nature02954.pdf.

Zitelli, et al. "Mass cultivation of *Nannochloropsis* sp. In annular reactors" Journal of Applied Phycology vol. 15, p. 107-113, Mar. 2003. Entire document, especially: abstract; p. 110, col. 1-2 [online]. Retrieved from the Internet on [Oct. 5, 2010]. Retrieved from: <URL: http://www.springerlink.com/content/v77772k1mp081775/ fulltext.pdf.

Csogor, et al. "Light distribution in a novel photobioreactor—modeling for optimization" Journal of Applied Phycology, vol. 13, pp. 325-333, May 2001, Entire document, especially: abstract; p. 110, col. 1-2 [online]. Retrieved from the Internet on [Oct. 5, 2010]. Retrieved from: <URL: http://www.springerlink.com/content/p77j66g3j2133522/fulltext.pdf.

Sukenik, et al (Journal of Psychology. Jun. 2000; 36(3): 563-570).

Genbank Accession No. U71602 (*Nannochloropsis sp. Violaxnthin*/chlorophyll a binding preotein precursor (NANVCP) mRNA), 1996.

Relationship Development in Communiy-Based and School-Based Programs [PDF] C Herrera, CL Sipe, WS McClanahan . . . mentormap.org Apr. 2000.

Abe, et al., AG610981, *Musmusculus molossinus* DNA, 2004.

Kopczynski, et al., CO268749, *Drosophila melanogaster* cDNA clone EK092604, 2004.

Prein, et al. FEBS Letters 485 (2000) 29-34.

Wendland, et al., Curr. Gen. (2003) 44:115-123.

Kindle, et al., J. Cell. Biol., (1989), 109:2589-2601.

Thiel et al. Transformation of a *Filamentous Cyanobacterium* by Electroporation. Journal of Bacteriology. Oct. 1989, vol. 171, No. 10, pp. 5743-5746, especially p. 5743, abstract, p. 5744, left column, first paragraph, Fig 1.

Shi, et al. Analysis of expressed sequence tags from the marine microalga *Nannochloropsis oculata* (*eustigmatophyceae*) J Phycol v 44, p. 99-102; abstract [online]: download from: http://www3.interscience.wiley.com/journal/119393460/abstract?CRETRY=1 &SRETRY=0 downloaded on Oct. 23, 2009. In support of publication date of shi et al. as Feb. 6, 2008.

Collins, et al., "Strategic human resource practices, top management team social networks, and firm performance," Academy of Management Journal, 2003-vol. 46 : 740-751.

Shi, et al. Analysis of expressed sequence tags from the marine microalga *Nannochloropsis oculata* (*eustigmatophyceae*) J Phycol v 44, p. 99-102; abstract.

Prein et al. "A Novel Strategy for Constructing N-Terminal Chromosomal Fusions to Green Fluorescent Protein in the Yeast *Saccharomyces cerevisiae*," FEBS Letters 485 (2000) 29-34.

Wendland "PCR-Based Methods Facilitate Targeted Gene Manipulations and Cloning Procedures," Curr. Gen. (2003) 44: 115-123.

Kindle "Stable Nuclear Transformation of *Chlamydomonas* Using the *Chlamydomonas* Gene for Nitrate Reductase," The Journal of Cell Biology, vol. 109 (No. 6, Pt.1), Dec. 1989 2589-2601.

* cited by examiner

100

102 → GGGGGTCTTTTGTCCTTTCCTCTATAGCCCACCCGTCTAGAGGGCACACGCGATGATCTTTATATCTCTTC
ATGTGTCTTTGTTTAACTAGGATACTGCCGGGTGAATGCCCATGCGGACAAGAGGCCAAACTCTATCTACA
CCCTTTGACTTCTCTGTGTGCTGTAGTGTGCTTGCATGCCCTGAAAGTCCAGGCATCCCACTTGTGCT
CTAACCCCATTCAAAACACAGCAGAAGTGCTTAATTAAGATATAGATTCATGATCTCCTGTCCCCTCCTTCTT
ACCTTTTCACAAACCTC

104 → ACACAGAAGTCTCCACTCTTCGCCCTCTAAAACCTCTTTTAAATT

106 → ATGGTAAGTTCGTGCGGCAGTGGGTTTTCGGATCTATATATTTGTCAAGATCCAGTTCAAGGTCAGGGATGTA
GATTAAGTACAGAAGGAGAAGCACAAGCCGGCCAGTTCGCCCTCACGGCCCTGGAGCAGGGCATTTAATCC
CTCTATCTTACCAGAACCATACTATACAACCAATCCTGTTGCCATCGCTCTGTCTATTTGTCGTGCGTGCA
TGTGTCCATGGTGTGTGGGGGCAGGGTTTTCGGGGTTGCGGTTGAAGGCACCTTATCAGAAAGATGCC
CTCAGAGATAGAGGTAGCCCCCCCCGATCTTCGACCAGTCCTGTCAGGCGAACACTTTCACCGTCG
TTCACCTCGTTACACACAAGGAGTAGACCTCTGAAGTTCTAATTGTCATAAATGCCCCTCCCCCCTCCCTC
TTTCCCTTGATCTTCCCCCTCCGAGCAGATTATG

108 → GCCAAGTTGACCAGTGCCGTTCCGGTGCTCACCGCGCGACGTCGCCGAGCGGTCGAGTTCTGGACCGA
CCGGCTCGGGTTCTCCCCGGACTTCGTCGAGGACGACTTCGCCGTGTGCTCCGGACGACGTGACCCTGT
TCATCAGCGCGGTCCAGGACCCAGTGGTCCGGACACAACACCCTGGCCTGGGTGTGGCCGGCCTGGAC
GAGCTGTACGCCGGAGTCGGGAGGCGGGAGTTCGCGTGTCCACGAACTTCCGGGACCTCCGGGCGCCGA
GATCGGCGAGCAGCCGTGGGGGCGGAGTTCGCCTGCAGCCCGGCCAACTGCGTGCACTTCGTGG
CCGAGAGCAGGACTAA

110 → GCTTCTGTGGAAGAGCCAGTGGTAGTAGCAGTAGCAGCAGTAGCAGCCGCAGCACTCAGTGTTGGCGC
GAGAGATTGTCCATCCTCTTCTAACCTACCGGAAGAGATAAGGCCCTTTCTCCCGTAGCTGTCTTCGTTT
GTTTGTGCTTGATTGCTTGATATGAGAGTGTTGAATTCCAGAGTTGATCATGTTTTCTCTGTCCTTCCTAC
CCCGTCATTTCATTTCTTTCTCCCTGGTTCTCTTTGTCACCCTTATTTACATAAAATTTCTTTGTTTAT
AGTGAGAGGAAGGTAGAGAGGCATTGAGAGTGGAGCCGGGGAAAAGGCTTGTGTGTTGTCTTTGAAAAAGTTGT
AGAAACAGATCTGTTGAGCATTGAGAGTGGACCTCTTTCACTACATGTGATGGAGAAACAAAAGTGA
TTAAATCACGAATCCGTTAGTTCTCATGTTCTCATGTACCTCTTTCACTACATGTGATGGAGAAACAAAAGTGA
GGATTAATTGAAGAAAAAGAAGAGTTCGACACGTCAAAACCGCCCAAAAGACGTCACAAAGAACTTGATT
CTCTTTGCCGTGTTGATCCGTCTTTTCCCCAGCTTTCTTTGCCACCCGTGGCACCGTGGCACACAGAGATGACAAGA
TCAG

FIG. 1

TRANSFORMATION OF ALGAL CELLS

CROSS-REFERENCE TO RELATED APPLICATIONS

The present application claims the benefit and priority of U.S. Provisional Patent Application Ser. No. 61/059,672 filed on Jun. 6, 2008, titled "VCP-Based Vector for *Nannochloropsis* Transformation," which is hereby incorporated by reference.

The present application is related to U.S. Non-Provisional patent application Ser. No. 12/480,635 filed on Jun. 8, 2009, titled "VCP-Based Vectors for Algal Cell Transformation," which is hereby incorporated by reference.

REFERENCE TO SEQUENCE LISTINGS

The present application is filed with sequence listing(s) attached hereto and incorporated by reference.

BACKGROUND OF THE INVENTION

1. Field of the Invention

This invention relates to molecular biology, and more specifically to the transformation of algal cells.

2. Description of Related Art

Transformed algae cells may be useful in aquaculture production. The transformation of small algal cells with strong cell walls, however, is difficult to achieve. Accordingly, there is a need for improved methods of algal cell transformation.

SUMMARY OF INVENTION

Exemplary methods include a method for transforming an algal cell by preparing a transformation construct, preparing a particle for bombarding the algal cell, adhering the transformation construct to the particle, bombarding the algal cell with the particle, and growing the algal cell into a colony. The transformation construct is replicated within a nuclear genome of the algal cell and the growing of the algal cell is in a nutrient medium.

Another exemplary method may include a method for genetically modifying an algal cell, by adding nucleic acid to the algal cell while the algal cell is suspended in a solution of low conductivity, introducing the nucleic acid into the algal cell by application of an electrical pulse resulting in a transformed algal cell, and selecting a colony that includes the transformed algal cell.

BRIEF DESCRIPTION OF THE DRAWINGS

FIG. 1 shows a sequence of an exemplary transformation construct.

DETAILED DESCRIPTION OF THE INVENTION

Figure 2:
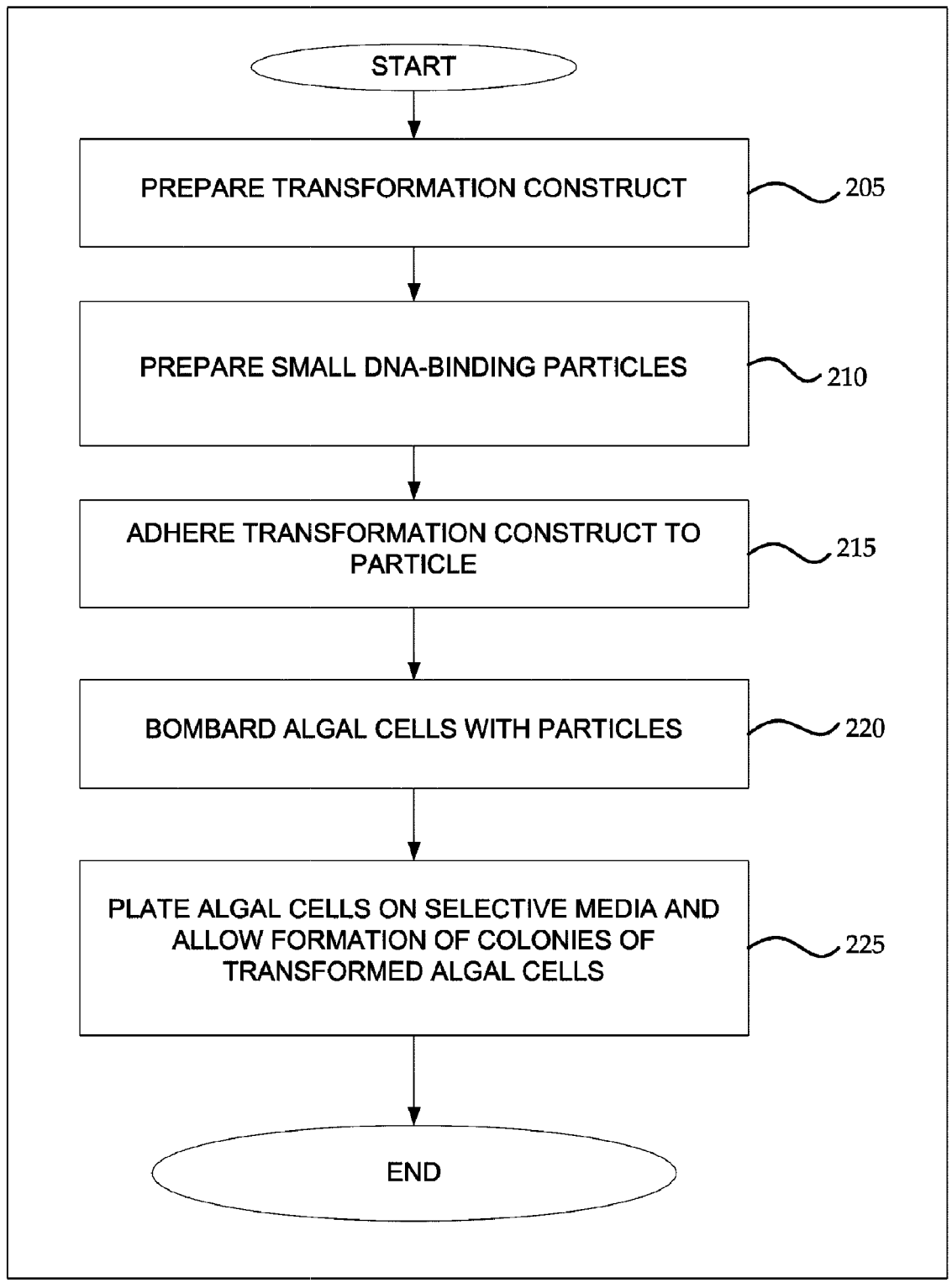
FIG. 2 illustrates an exemplary method for transforming an algal cell with a particle gun.

Provided herein are exemplary methods for transforming algal cells. Transformed algae cells may be useful in aquaculture production. The transformation of small algal cells with strong cell walls, however, is difficult to achieve. Various exemplary embodiments of the present invention are useful in the efficient transformation of *Nannochloropsis*, a microalga of about 3-5 micrometers in size.

Typically, gold particles having a size of about 0.6 micrometers are used in biolistic transformation of algae smaller than about 5 micrometers. A transformation vector or transformation construct is precipitated onto the gold particles, and the gold particles carrying the transformation construct are propelled through the cell walls of the algae. The transformation efficiency of *Nannochloropsis* with this method is very low.

According to the various exemplary methods provided herein, aggregates of gold particles are broken into smaller fragments to increase transformation efficiency. Using a 1510 Branson Bath Sonicator, 0.6 micrometer gold particles are sonicated for one hour just prior to precipitating a transformation construct onto the gold particles. Using the sonicated gold particles or beads, fourteen micrograms of transformation construct may produce approximately twenty zeocine resistant transformants. Thus, this exemplary embodiment provides about a twenty-fold increase in transformation efficiency over currently available methods.

An alternative exemplary embodiment uses an improved electroporation method to transform algal cells. In electroporation, algal cells are subjected to an electric current that opens transient pores in the membranes of the algal cells. A transformation vector may pass through an open pore, eventually leading to the successful transformation of the algal cell. Using a Biorad Genpulser I electroporator set to the exponential protocol, the following electroporation conditions were used: 2200V, 500Ω shunt resistor, 50 µF capacity, 2 mm gap cuvette. When $10^9$ cells have been used in iso-osmotic non electrolyte buffer (resistance higher than 1100Ω) in a volume of 100 microliters, typical time constants τ of 20-24 ms have been reported by the device. This approach produced hundreds of zeocine resistant transformants per microgram of transformation construct used.

FIG. 1 shows the sequence of an exemplary transformation construct. The exemplary transformation construct 100 includes a promoter sequence 102, DNA encoding a transcribed but untranslated 5' region ("UTR") 104, an intron 106, a ble gene 108 and DNA encoding a 3' UTR 110. The transformation construct may comprise any number of promoters, genes, and/or other nucleic acid polymers (naturally occurring or synthetic) and/or their analogs, or other compounds that do not interfere with the ability of the transformation construct to enter the algal cell or the algal genome, or to function. In some embodiments, additional nucleotides may appear in the transformation construct to facilitate or direct the insertion of the construct (or any part thereof) into a desired location in the genome.

The various exemplary methods described herein may be employed using the exemplary transformation vectors or transformation constructs PL90, H8 and B9 as described in U.S. Non-Provisional Patent Application Ser. No. 12/480,635 filed on Jun. 8, 2009, titled "VCP-Based Vectors for Algal Cell Transformation," which is hereby incorporated by reference. The difference between the three exemplary vector constructs is the type of selection marker gene (SG) used: the sh ble gene (PL90), the hygromycin B phosphotransferase gene (H8), or the blastocidin S deaminase (B9) gene.

FIG. 2 illustrates an exemplary method for transforming an algal cell with a particle gun.

At step 205, a desired transformation construct is prepared. According to one exemplary embodiment, the transformation construct may be either the PL90 transformation vector, the H8 transformation vector, or the B9 transformation vector.

At step 210, small DNA-binding particles are prepared. According to one exemplary embodiment, 0.6 µm gold particles are sonicated in buffer for one hour.

At step 215, the transformation construct is adhered to the small DNA-binding particles. In one exemplary method, transformation constructs are precipitated onto the gold particles.

At step 220, algal cells are bombarded with the gold particles having the transformation constructs precipitated onto them. *Nannochloropsis* cells, according to one exemplary method, are bombarded with fourteen micrograms of transformation construct DNA that has been precipitated onto 0.42 mg of the 0.6 µm gold particles.

At step 225, the algal cells are grown into colonies on selective medium. According to one exemplary embodiment, if the transformed cells produce a large quantity of a desired gene product, the cells may be further processed to collect the desired product. One having ordinary skill in the art will recognize that many appropriate buffers, media, and/or methods of product collection may be used.

EXAMPLE ONE

*Nannochloropsis oceanica* cells were grown in low light (85 µE/(m2*s)) to mid log phase in F2 media, 50% seawater (See e.g., Guillard, R. R. L. and Ryther, J. H. 1962. Studies of marine planktonic diatoms. I. Cyclotella nana Hustedt and Detonula confervacea Cleve. Can. J. Microbiol. 8: 229-239). *Nannochloropsis* cells were then pelleted at 2500 g for 15 min. The pellet was then resuspended in fresh media. 5*10^9 resuspended cells were spread on petri dishes (F2 media, 50% seawater, 1% Bactoagar™ from DIFCO) and allowed to dry. 0.6 µm gold particles (Biorad) were coated essentially as recommended by Biorad with transformation vector PL90. The plated cells were then bombarded with microparticles (coated with transformation construct DNA as recommended by Biorad) by a particle gun (Biolistic PDS-1000/He particle gun Bio-Rad) at vacuum pressure of 29 mm Hg utilizing the heptameric adapter from Biorad. All different stages were used in combination with 3 different rupture discs (1100 PSI, 1350 PSI, 1550 PSI) provided by Biorad. Cells were subsequently resuspended in 10 ml fresh F2 Medium (half salinity) and allowed to recover overnight under low light (~10-25 µE/(m2*s)). 0.5*10^7 cells were then plated on agar plates (0.8% Bactoagar™ from DIFCO) containing the selection agent (2 µg/ml zeocine, µg/ml 300 hygromycin or 50 µg/ml blasticidin, depending on the transformation construct used) and incubated at 25° C. at ~50 µE/(m2*sec). Negative control DNA was linearized pJet1 vector DNA (Fermentas). Growth of colonies could be observed after ~2-3 weeks. Colonies were then analyzed for the presence of the selection marker gene. Colonies on selective media were never obtained in experiments utilizing the control DNA. Only utilization of 1350 PSI rupture disc, stage 1 (uppermost stage, just underneath heptameric adapter) and 1550 PSI rupture disc stage 2 yielded a few transformants under these conditions.

To proof for the presence of transformation construct within the cells (and thus that the transformation experiment was a success), a single colony was picked and restreaked on unselective medium and allowed to grow for approximately one week. Cells were then scraped (~10 µg cells), washed 3 times in F2-50% seawater, incubated with 30 units DNAse I in DNAse I buffer (Fementas) 1 hour at 37° C. Cells were then washed once in F2-50% seawater and resuspended in 50 µl F2-50% seawater. Cells were pelleted and the supernatant collected; cells were resuspended in 50 µl ddH20. Cell and supernatant fractions were incubated 7 minutes at 95° C.; 5 µl each fraction were subjected to PCR (50 µl reaction volume) with specific primers against the ble gene (rev: 5'TTA GTC CTG CTC CTC GGC CAC GAA3', for: 5'ATG CCC AAG TTG ACC ACT GCC GT3').

The PCR program was:
1. 94 C, 3 min, 1 cycle;
2. 94 C, 15 sec;
3. 58 C, 30 sec;
4. 72 C, 30 sec (steps 2-4 are amplification stage, 38 cycles);
5. 72 C, 5 min; and
6. 4 C, cool down and keep temperature.

Figure 3:
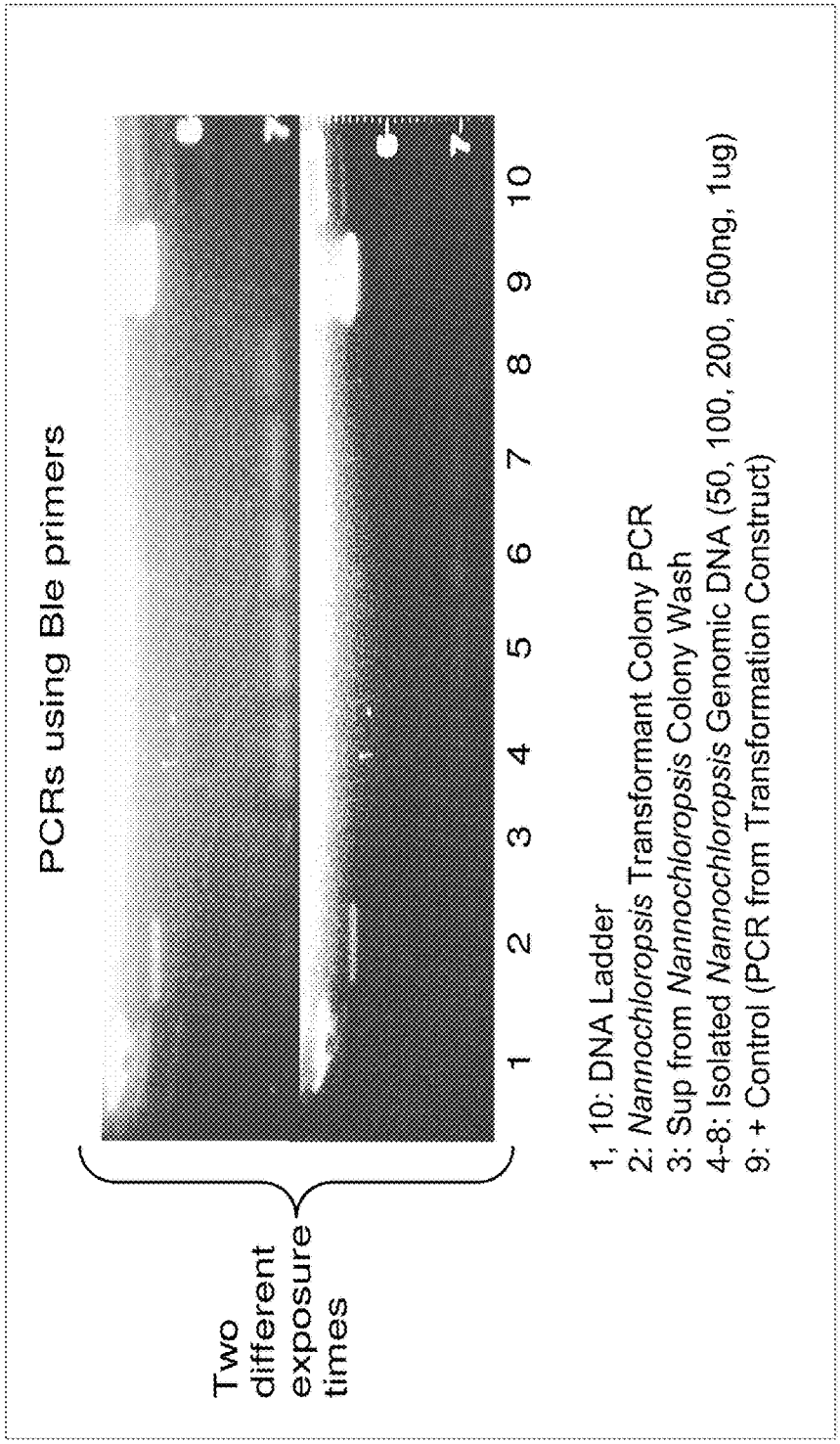
FIG. 3 shows an exemplary polymerase chain reaction result obtained using ble primers as described in connection with Example One.

FIG. 3 shows the exemplary polymerase chain reaction result obtained using ble primers as described in connection with Example One.

EXAMPLE TWO

We followed the procedures of Example One, except this time utilizing a 1510 Branson Bath Sonicator, 0.6 µm gold particles were sonicated for 1-hour just prior to DNA precipitation onto beads. Using the sonicated beads, 14 µg DNA produced approximately 20 zeocine-resistant transformants.

Detailed Procedure.

Growth and preparation of cells: the cells were grown in 2 L flasks in F2 medium (containing seawater of half salinity) to early log phase. The cells were then harvested by centrifugation for 10 min. at 2500 and gently resuspended in fresh F2 medium. 5*10^9 cells (in ~400 µl) were then plated on an agar plate (containing 1% Bactoagar™ from DIFCO) and allowed to dry for ~20 minutes in a sterile hood.

Preparation of Particles.

Different sizes and materials of particles were used (all obtained from Biorad), i.e. Tungsten particles 0.7 and 1 µm average diameter and gold particles 1 µm or 0.6 µm average diameter. Prior to the precipitation of the DNA onto the particles (the micro carrier), the particles were resuspended in ddH2O and sonicated for 1 hour in a 1510 Branson Bath Sonicator. 3 mg particles were coated with 100 µg linearized transformation construct DNA as described elsewhere (see user manual Biolistic PDS-1000/He particle gun from Bio-Rad) and resuspended in 500 µl Ethanol after 2 washing steps in the same volume ethanol. 10 µl of this DNA coated particle solution ('the microcarrier') was pipetted onto each macro-carrier which was fitted subsequently into the Hepta Adapter (optional component of the Biolistic® PDS-1000/He Particle Delivery system). Thus, each shot with the particle gun provided 7×2 µg=14 µg DNA precipitated on micro carrier. Coated particles were used for biolistic transformation within an hour.

Delivery of Particles to Cells.

The petri dish containing the cells was placed on the corresponding stage within the particle delivery system (stage 1 being the nearest to the heptamer adapter, stage 3 being the one most far away). One of three different rupture discs (Biorad) was used: 1100 psi, 1350 psi, 1550 psi. Vacuum was generally applied to 29 mm Hg (obtained within ~20 sec.) and the He pressure was increased at max speed in order to provide the He shock wave after rupture of the rupture disc. The pressure in the delivery chamber was instantly increased at maximal rate (less than 10 sec until atmospheric pressure was reached) and the petri dish with the bombarded cells was recovered.

Post Delivery Treatment of Cells.

The cells were gently scraped off the plate resuspended in 10 ml of F2 medium (half salinity compared to seawater) and allowed to recover in low light (~10 µE/(m2*s)) over night. Next day, 0.5*10^7 cells were plated on F2 agar plates (petri dish, F2 medium with half salinity compared to seawater and 0.8% Bactoagar™ from DIFCO) and the respective selection agent. Plates were incubated at 25° C. at 50 µE/(m2*sec). Colonies were visible after ~2-3 weeks.

Results.

1. From all the particles tested, only the 0.6 µm gold particles produced transformants.
2. We tested all different combinations of stage position (within the particle delivery system) and rupture disc.
3. A major difference was observed when we pretreated the gold particles with ultrasound.

The following table reflects the quantity of transformants observed when using different experimental parameters. The vector used in these experiments was PL90 conferring resistance against the drug zeocine.

| | Gold particles pretreatment[1] | | | | | |
|---|---|---|---|---|---|---|
| | no | no | no | yes | yes | yes |
| | | | Rupture disc | | | |
| | 1100 psi | 1350 psi | 1550 psi | 1100 psi | 1350 psi | 1550 psi |
| Stage 1 | 0 | 1 | 0 | 11 | 4 | 77 |
| 2 | 0 | 0 | 2 | 25 | 4 | 22 |
| 3 | 0 | 0 | 0 | 8 | 4 | 5 |

[1] gold particles were washed and then disrupted by 1 h ultra sound treatment

These results indicate that:

1. Pretreatment of the 0.6 µm gold particles by ultra sound dramatically increases the transformation efficiency.
2. That the transformation efficiency is highest at 1100 Psi pressure (rupture disc) and if the petri dish containing the cells is localized on stage 2.
3. The vector PL90 may be used for the nuclear transformation of *Nannochloropsis* by conferring resistance against the drug zeocine.

Figure 4:
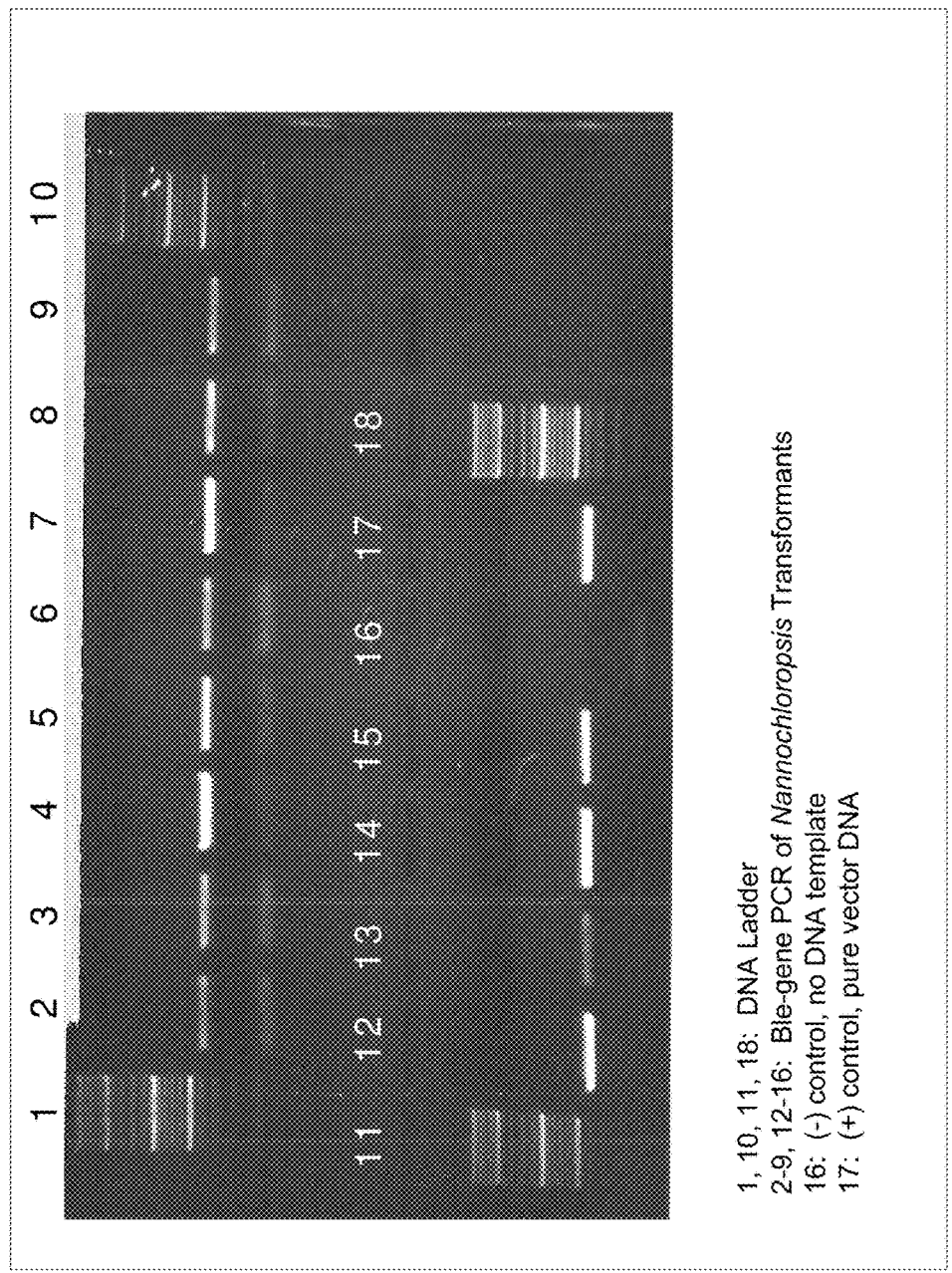
FIG. 4 shows the exemplary polymerase chain reaction result obtained as described in connection with Example Two.

FIG. 4 shows the exemplary polymerase chain reaction result obtained as described in connection with Example Two.

EXAMPLE THREE

Transformation via Electroporation.
Detailed Procedure.
Growth and Preparation of Cells.

*Nannochloropsis oceanica* was grown in 2 L flasks in F2 medium (containing seawater of half salinity) to mid log phase. The cells were then harvested by centrifugation for 10 min. at 2500 and gently resuspended in 375 mM sorbitol. The cells were washed several times in 375 mM sorbitol solution in order to minimize conductivity of remaining medium. The cells were finally resuspended to a final concentration of 10^10 cells/ml and used for transformation within an hour.

Electroporation.

Electroporation was performed in a Biorad GenPulser I Electroporator utilizing 2 mm cuvettes. 100 µl cells at 10^10 cells/ml were pipetted into a 2 mm cuvette and varying amounts of transformation construct in <5 µl volume ddH2O added. The cuvette containing the DNA-cell mixture was gently snipped for mixing and then placed into the electroporation chamber.

Device settings were exponential decay protocol with 500 Ohm Shunt resistance and 50 µF capacity, 2 mm Gap Post Delivery Treatment of Cells.

After electroporation the cells were allowed to stay in the cuvette for 3 minutes before they were recovered and resuspended in 10 ml F2 medium (half salinity). After an overnight incubation in low light (~10 µE/(m2*s), 0.5*10^7 cells were plated on F2 agar plates and the respective selection agent. Plates were incubated at 25° C. at 50 µE/(m2*sec). Colonies were visible after ~2-3 weeks.

Results.

In initial experiments, we used 0.5 µg DNA/100 µl cell suspension and varied the voltage. We routinely measured electrical resistance of the cell-DNA mixture with the respective option in the Biorad GenPulser I Electroporator to ensure that resistance was >1100 Ohm. The actual electroporation usually returned exponential decay times τ of 20-24 ms. Initially, when performing these experiments with varying field strengths we got a single transformant (again we used the PL90 vector linearized and performed selection on agar plates containing zeocine) at the highest field strength initially tried (which was 1000V, =5 kV/cm). 5 kV/cm is a very high field strength and we did not expect that we might obtain transformants at all at such a high field strength. Since we obtained a single transformant at this high voltage we performed electroporations in additional experiments at very high voltages.

Figure 5:
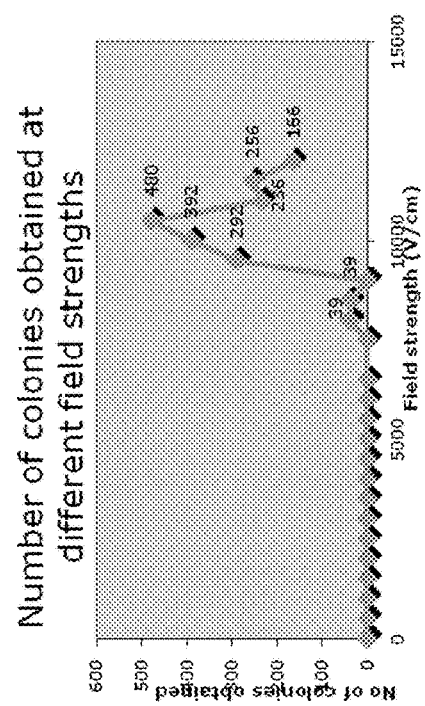
FIG. 5 shows the number of algal cell transformants obtained based on the field strength of electroporation applied to perform the transformation as described in connection with Example Three.

FIG. 5 shows the number of algal cell transformants obtained based on the field strength of electroporation applied to perform the transformation as described in connection with Example Three. The result of this experiment as shown in FIG. 5 was very surprising: transformation was successful at field strengths equal or higher than 8 kV/cm and efficiency peaked at 10.5 kV/cm. Note that applied field strengths for the electroporation of algae are typically factor 10 lower. Higher Field strengths than 12000V/cm were not possible to apply (cuvettes arced).

We conclude that we can transform *Nannochloropsis* with the vector PL90 if we treat the cells as indicated above.

EXAMPLE FOUR

Ideal Electroporation.

Parameters are (within Biorad GenPulser I Electroporator): 10^9 cells in 100 µl 375 mM sorbitol (washed several times), 500 Ohm shunt resistor, 2 mm gap cuvette, 10500 volt/cm (=2100V/2 mm), exponential decay program.

We then tested the efficiency of transformation by adding varying amounts of DNA to the electroporation cuvette (again containing 10^9 cells in 100 µl).

Figure 6:
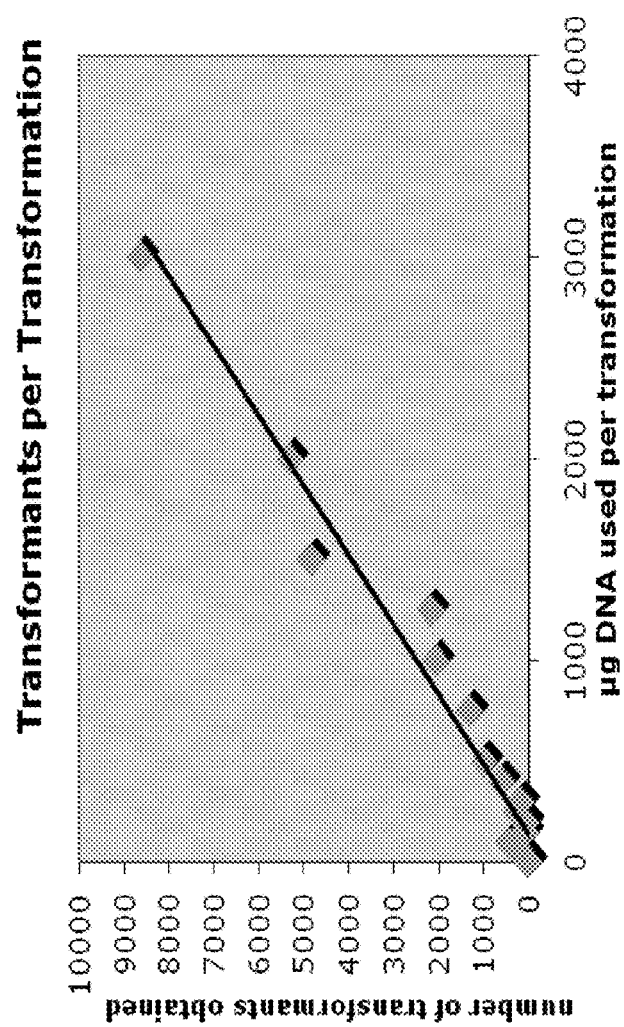
FIG. 6 shows the number of transformants obtained under exemplary optimal electroporation conditions, while varying the amount of transformation construct DNA used as described in connection with Example Four.

FIG. 6 shows the number of transformants obtained under exemplary optimal electroporation conditions, while varying the amount of transformation construct DNA used as described in connection with Example Four. We observed a linear increase in the number of transformants obtained based on increasing the amount of transformation construct DNA used. For example, 3 µg of transformation construct DNA added during a single electroporation experiment yielded approximately 9000 transformants, 1.5 µg of transformation construct DNA yielded approximately 4500 transformants.

This result indicates that no saturation with DNA occurred and that the transformation method via electroporation which we established is extremely efficient.

Figure 7:
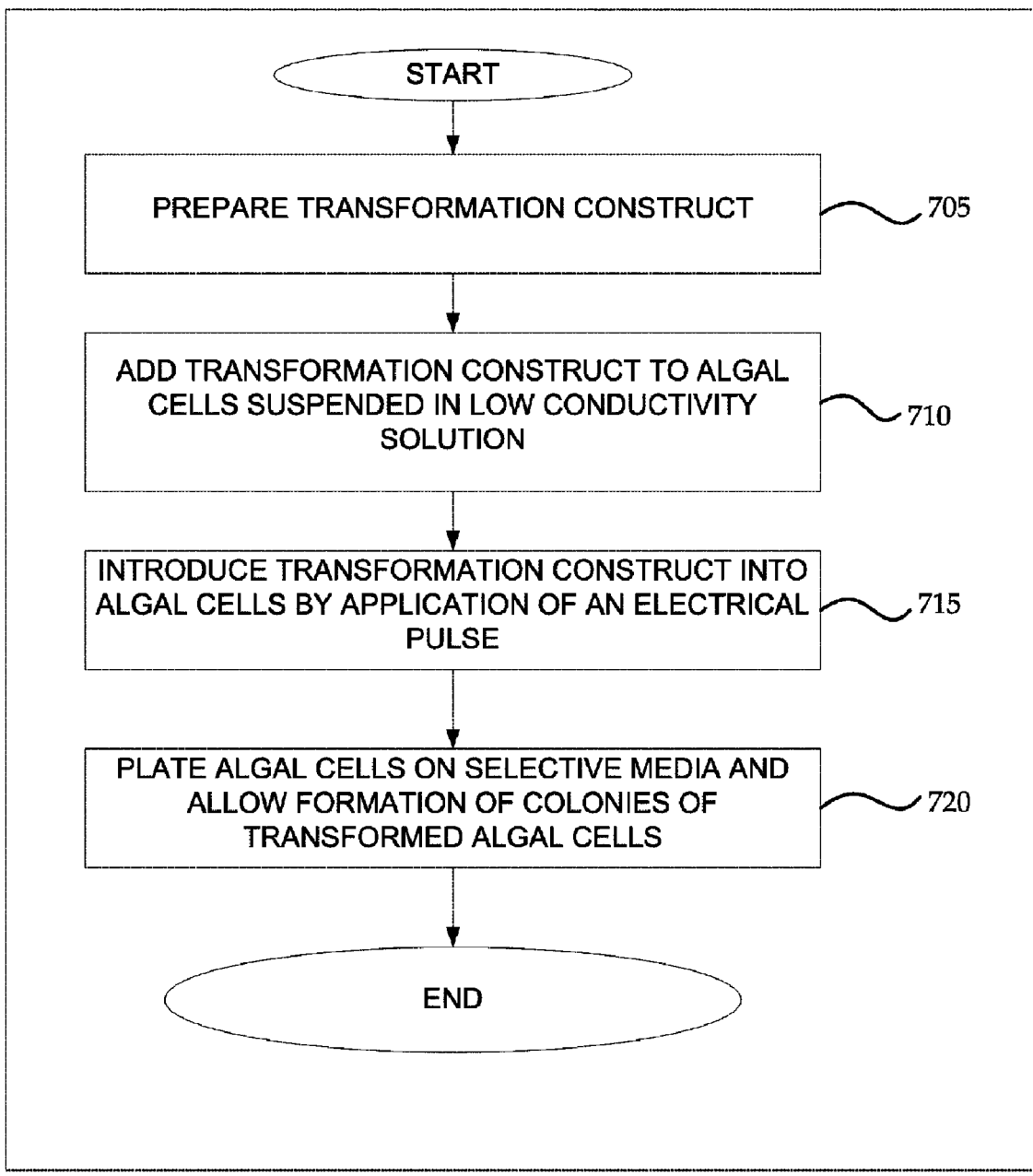
FIG. 7 illustrates an exemplary method for transforming an algal cell with electroporation.

FIG. 7 illustrates an exemplary method for transforming an algal cell with electroporation.

At step 705, a desired transformation construct is prepared. According to one exemplary embodiment, the transformation construct may be either the PL90 transformation vector, the H8 transformation vector, or the B9 transformation vector.

At step 710, the transformation construct is added to algal cells, while the algal cells are suspended in a solution of low conductivity. In various exemplary embodiments, the solution is a sorbitol solution.

At step 715, the transformation construct is introduced into the algal cells by application of an electrical pulse, resulting in transformation of the algal cells. According to some exemplary embodiments, the electrical pulse is applied with a field strength of higher than approximately 10,000 V/cm, and with a shunt resistor of greater than approximately 100 OHM.

At step 720, the algal cells are grown into colonies on selective medium. According to one exemplary embodiment, if the transformed cells produce a large quantity of a desired gene product, the cells may be further processed to collect the desired product. One having ordinary skill in the art will recognize that many appropriate buffers, media, and/or methods of product collection may be used.

While various embodiments have been described above, it should be understood that they have been presented by way of example only, and not limitation. Thus, the breadth and scope of a preferred embodiment should not be limited by any of the above-described exemplary embodiments.

What is claimed is:

1. A method for transforming an algal cell, the method comprising:
   preparing a transformation construct, the transformation construct including a gene involved in lipid biosynthesis;
   preparing a particle for bombarding the algal cell;
   adhering the transformation construct to the particle;
   bombarding the algal cell with the particle;
   growing the algal cell into a colony;
   wherein the particle is a gold particle smaller than or equal to approximately 1 micrometer average diameter; and
   wherein the preparing of the gold particle includes sonicating the gold particle with ultrasound prior to the adhering of the transformation construct to the gold particle.

2. The method of claim 1, wherein the transformation construct is replicated within a nuclear genome of the algal cell.

3. The method of claim 1, wherein the growing of the algal cell is in a nutrient medium.

4. The method of claim 1, wherein the transformation construct is a nucleic acid in an expression cassette.

5. The method of claim 4, wherein the expression cassette further comprises:
   a promoter functional in the algal cell operably linked to the gene involved in lipid biosynthesis;
   a selectable transformation marker gene; and
   a termination region functional in the algal cell operably linked to the gene involved in lipid biosynthesis.

6. The method of claim 5, wherein the selectable transformation marker gene is a gene capable of conferring antibiotic resistance to the algal cell.

7. The method of claim 6, the method further comprising: selecting the algal cell growing in a selective medium having an antibiotic the gene has conferred resistance upon to the algal cell.

8. The method of claim 1, wherein the algal cell is an auxotrophic mutant.

9. The method of claim 1, wherein the transformation construct includes a sh ble gene.

10. The method of claim 1, wherein the transformation construct includes a hygromycin B phosphotransferase gene.

11. The method of claim 1, wherein the transformation construct includes a nitrate reductase gene.

12. The method of claim 1, wherein the transformation construct includes a blastocidin S deaminase gene.

13. The method of claim 1, wherein the adhering of the transformation construct to the particle includes precipitating DNA of the transformation construct to the particle.

* * * * *

UNITED STATES PATENT AND TRADEMARK OFFICE
CERTIFICATE OF CORRECTION

PATENT NO.          : 8,119,859 B2
APPLICATION NO.     : 12/480611
DATED               : February 21, 2012
INVENTOR(S)         : Bertrand Vick et al.

Page 1 of 1

It is certified that error appears in the above-identified patent and that said Letters Patent is hereby corrected as shown below:

At column 1, line 58, please italicize the word "ble".
At column 2, line 53, please italicize the word "ble".
At column 2, line 53, please put in bold font the number "110".
At column 3, line 4, please italicize the words "sh ble".
At column 4, line 13, please italicize the word "ble".
At column 4, line 25, please italicize the word "ble".
At column 4, line 48, please delete the words "micro carrier" and replace them with the word "microcarrier".
At column 4, line 59, please delete the words "micro carrier" and replace them with the word "microcarrier".
At column 5, line 44, please delete the words "ultra sound" and replace them with the word "ultrasound".
At column 6, line 10, please add a period after the word "Gap".
At column 6, line 43, please delete the word "Field" and replace it with the word "field".
At column 10, line 29, in claim 9, please italicize the words "sh ble".

Signed and Sealed this
Fifth Day of March, 2013

Teresa Stanek Rea
*Acting Director of the United States Patent and Trademark Office*

SEQUENCE LISTING

```
<160> NUMBER OF SEQ ID NOS: 1

<210> SEQ ID NO 1
<211> LENGTH: 1820
<212> TYPE: DNA
<213> ORGANISM: Nannochloropsis

<400> SEQUENCE: 1
ggcggtcttt tgtcctttcc tctatagccc acccgtctag agggcacacg cgatgatctt      60
tatatctctt catgtgtctt tgttttaact aggatactgc cgggtgaatg cccatcggac     120
aagaggccaa actctatcta caccctttg acttctgttg tggtcgtagt gtgtgcttgc     180
atgccctgaa agtccaggca tcccacttgt gctctaaccc cattcaaaac agcagaagtg     240
cttaattaag atatagattc atgatctcct gtcccctcct tcttacctt tcacaaacct     300 cacacagaag tctccactct tcgcctctaa aacctctttt taaattatgg taagttcgtg     360
cggcagtggg ttttcggatc tatatttgtc aagatccagt tcaaggtcag ggatgtagat     420
taagtacaga aggagaagca caagcgcgcc agttcgcccc tcacggcctg gagcagggca     480
tttaatccct ctatcttacc agaaccatac tatacaacca atcctgttgg catcgctctg     540
tctatttgtc gtgcgtgcat gtgtccatgg tgtggtgggg ggcaggggtt ttcggggttg     600
cggttgaagg caccttatca gaaagatgcc ctcagagata gaggtagccc cctcccccg     660 atcttcgacc agtcctgtca ggcgaacact ttcacccgtc gttcacctcg ttacacacaa     720
ggagtagacc tctgaagttc taattgtcat aaatgccccc ccccctccc tcttccctt     780 gatcttcccc tccgagcaga ttatggccaa gttgaccagt gccgttccgg tgctcaccgc     840
gcgcgacgtc gccggagcgg tcgagttctg gaccgaccgg ctcgggttct cccgggactt     900
cgtggaggac gacttcgccg gtgtggtccg ggacgacgtg accctgttca tcagcgcggt     960
ccaggaccag gtggtgccgg acaacaccct ggcctgggtg tgggtgcgcg gcctggacga    1020
gctgtacgcc gagtggtcgg aggtcgtgtc cacgaacttc cgggacgcct ccgggccggc    1080
catgaccgag atcggcgagc agccgtgggg gcgggagttc gccctgcgcg acccggccgg    1140
caactgcgtg cacttcgtgg ccgaggagca ggactaagct tctgtggaag agccagtggt    1200
agtagcagta gcagcagcag tagcagccgc agcactcagt gttggcgcga gagattgtcc    1260
atcccttctt aacctaccgg aagagaaata aggcctttct cccgtagctg tcttcgtttg    1320
tttgtgctga ttgcttgata tgagagtgtt gaattcctgc atcatgtttt tctctgtagt    1380
cctttcctac ccccgtcatt ttctttctc cctggttctt cttttgtcac ccttatttta    1440
```

```
cataaaattt tctttgttta tagtgagagg aaggtagaga ggggaaaaca agaacaacga    1500
acgcaagcgt gtgaaaggag ggcgagtaga agagaaacag atctgttgag cattgagagt    1560
ggagccgggg gaaaggcttg tgtgttgtct ttgaaaaagt tgtttaaatc acgaatccgt    1620
tagttctcat gtgtacctct ttcactacat gtgatggaga aaacaaaagt gtgaggatta    1680
attgaagaaa aagaagagtt cgacacgtca aaccgcccaa aagacgtcac aaagagaact    1740
tgattctctt tgccgtgttg atcctgtctt ttcccccagc ttttcttgcc acccgtggca    1800
cacgagatgg acaagatcag                                                1820
```